(12) United States Patent
Chow et al.

(10) Patent No.: US 10,695,358 B2
(45) Date of Patent: Jun. 30, 2020

(54) ORAL REHYDRATION COMPOSITION WITH OLIGOSACCHARIDES

(71) Applicant: ABBOTT LABORATORIES, Abbott Park, IL (US)

(72) Inventors: Jomay Chow, Westerville, OH (US); Pedro Prieto, Columbus, OH (US); Ned McCoy, Dublin, OH (US)

(73) Assignee: ABBOTT LABORATORIES, Abbott Park, IL (US)

( * ) Notice: Subject to any disclaimer, the term of this patent is extended or adjusted under 35 U.S.C. 154(b) by 0 days.

(21) Appl. No.: 15/106,568

(22) PCT Filed: Dec. 19, 2014

(86) PCT No.: PCT/US2014/071578
§ 371 (c)(1),
(2) Date: Jun. 20, 2016

(87) PCT Pub. No.: WO2015/095747
PCT Pub. Date: Jun. 25, 2015

(65) Prior Publication Data
US 2016/0339046 A1 Nov. 24, 2016

Related U.S. Application Data

(60) Provisional application No. 61/919,004, filed on Dec. 20, 2013.

(51) Int. Cl.
| | | |
|---|---|---|
| *A61K 31/00* | (2006.01) |
| *A61K 9/00* | (2006.01) |
| *A61K 31/702* | (2006.01) |
| *A23L 33/16* | (2016.01) |
| *A23L 33/21* | (2016.01) |
| *A23L 2/52* | (2006.01) |
| *A23L 2/39* | (2006.01) |
| *A23L 29/30* | (2016.01) |
| *A23L 33/10* | (2016.01) |
| *A23L 33/125* | (2016.01) |
| *A61K 31/194* | (2006.01) |
| *A61K 31/7004* | (2006.01) |
| *A61K 31/717* | (2006.01) |
| *A61K 33/00* | (2006.01) |
| *A61K 33/14* | (2006.01) |
| *A61K 33/30* | (2006.01) |
| *A61K 35/741* | (2015.01) |
| *A61K 35/00* | (2006.01) |

(52) U.S. Cl.
CPC .............. *A61K 31/702* (2013.01); *A23L 2/39* (2013.01); *A23L 2/52* (2013.01); *A23L 29/30* (2016.08); *A23L 33/10* (2016.08); *A23L 33/125* (2016.08); *A23L 33/16* (2016.08); *A23L 33/21* (2016.08); *A61K 9/0095* (2013.01); *A61K 31/194* (2013.01); *A61K 31/7004* (2013.01); *A61K 31/717* (2013.01); *A61K 33/00* (2013.01); *A61K 33/14* (2013.01); *A61K 33/30* (2013.01); *A61K 35/741* (2013.01); *A23V 2002/00* (2013.01); *A61K 2035/115* (2013.01)

(58) Field of Classification Search
CPC ........ A23V 2002/00; A23V 2200/3202; A23V 2250/1642; A23L 2/39; A23L 2/52; A23L 29/30; A23L 33/10; A23L 33/16; A23L 33/21; A23L 33/125; A61K 9/0095; A61K 31/717; A61K 31/702; A61K 31/7004; A61K 31/194; A61K 2035/115; A61K 35/741; A61K 33/30; A61K 33/14; A61K 33/00

See application file for complete search history.

(56) References Cited

U.S. PATENT DOCUMENTS

| | | | |
|---|---|---|---|
| 4,312,856 A | 1/1982 | Korduner et al. |
| 5,733,579 A | 3/1998 | Wolf et al. |
| 5,780,094 A | 7/1998 | King |
| 7,883,874 B2 | 2/2011 | Gibson et al. |
| 8,202,842 B2 | 6/2012 | Sinclair et al. |
| 2002/0019991 A1 | 2/2002 | Prieto et al. |
| 2003/0134804 A1 | 7/2003 | King et al. |
| 2004/0265462 A1 | 12/2004 | Carlson |
| 2009/0041902 A1 | 2/2009 | Bialek |

(Continued)

FOREIGN PATENT DOCUMENTS

| | | |
|---|---|---|
| CN | 102429307 | 5/2012 |
| TW | 201138859 | 11/2011 |
| WO | 1997/002829 | 1/1997 |

(Continued)

OTHER PUBLICATIONS

Nakhla T., "Neutral oligosaccharide content of preterm human milk", British Journal of Nutrition, 1999, vol. 82, pp. 361-367. (Year: 1999).*

(Continued)

*Primary Examiner* — Satyendra K Singh

(74) *Attorney, Agent, or Firm* — Calfee, Halter & Griswold LLP

(57) ABSTRACT

The general inventive concepts are directed to compositions and methods for the prevention and treatment of dehydration. Provided herein are nutritional compositions including oral rehydration compositions. Certain embodiments of the nutritional compositions have an acidic pH, and comprise a digestible carbohydrate, sodium, citrate, and an oligosaccharide selected from a fucosylated oligosaccharide and an N-acetylated oligosaccharide.

17 Claims, No Drawings

(56) References Cited

U.S. PATENT DOCUMENTS

2011/0142962 A1    6/2011   Luebbers et al.
2012/0171165 A1    7/2012   Buck et al.

FOREIGN PATENT DOCUMENTS

| WO | 2010/059428 | 5/2010 | |
|---|---|---|---|
| WO | 2011/071684 | 6/2011 | |
| WO | WO2012076321 A1 * | 6/2012 | ........... A61K 31/702 |
| WO | 2013/025104 | 2/2013 | |

OTHER PUBLICATIONS

Nutrition During Lactation, National Academy Press, Washington, D.C. 1991, Committee on Nutritional Status During Pregnancy and Lactation, Institute of Medicine, National Academy of Sciences, ISBN: 0-309-53767-3, total 326 pages. (Year: 1991).*

Aachary A.A. et al., "Xylooligosaccharides (XOS) as an Emerging Prebiotic: Microbial Synthesis, Utilization, Structural Characterization, Bioactive Properties, and Applications", Comprehensive Reviews in Food Science and Food Safety, 2011, vol. 10, pp. 2-16. (Year: 2011).*

International Search Report and Written Opinion in PCT/US2014/052220 dated Nov. 27, 2014.

International Search Report and Written Opinion in PCT/US2014/071578 dated Mar. 20, 2015.

Requirement for Restriction/Election in U.S. Appl. No. 14/915,433 dated Sep. 15, 2016.

Office Action in CO Application No. 16-75853 dated Jun. 28, 2016.

Coppa et al., "Human Milk Oligosaccharides Inhibit the Adhesion to Caco-2 Cells of Diarrheal Pathogens: *Escherichia coli*, Vibrio cholerae, and *Salmonella fyris*," Pediatric Research, vol. 59, No. 3, 2006, pp. 377-382.

La Ferla et al. "Synthesis of building blocks of human milk oligosaccharides. Fucosylated derivatives of the lacto- and neolacto-series," Carbohydrate Research, vol. 337, No. 15, 2002, pp. 1333-1342.

Newburg et al., "Human Milk Glycans Protect Infants Against Enteric Pathogens," Annual Review of Nutrition, vol. 25, 2005, pp. 37-58.

Non-Final Office Action in U.S. Appl. No. 14/915,433 dated Jan. 18, 2017.

Office Action in U.S. Appl. No. 14/915,433 dated May 31, 2017.

Office Action in U.S. Appl. No. 14/915,433 dated Nov. 20, 2017.

Office Action in CO Application No. 16-75853 dated Dec. 12, 2017.

Office Action in U.S. Appl. No. 14/915,433 dated Jun. 12, 2018.

Office Action in U.S. Appl. No. 14/915,433 dated Dec. 26, 2018.

Office Action in TW Application No. 103130011 dated Aug. 22, 2018.

* cited by examiner

ORAL REHYDRATION COMPOSITION WITH OLIGOSACCHARIDES

CROSS-REFERENCE TO RELATED APPLICATIONS

This application is the U.S. national phase entry of PCT/US14/71578, with an international filing date of Dec. 19, 2014, which claims priority to and any benefit of U.S. Provisional Application No. 61/919,004, filed Dec. 20, 2013, the entire contents of which are incorporated herein by reference in their entirety.

TECHNICAL FIELD

The general inventive concepts are directed to compositions and methods for the treatment of dehydration, and more particularly to oral rehydration compositions and uses thereof.

BACKGROUND

Dehydration resulting from fever, diarrhea, vomiting, or combinations thereof, is a leading cause of morbidity and mortality in the developing world. While not generally considered a substantial worry for healthy individuals in developed countries, it remains a considerable health concern for those in poor or compromised health. One method for treating dehydration is administration of an Oral Rehydration Composition(s) (ORC). In general, when consumed by an individual afflicted with dehydration, an ORC supplies necessary calories and electrolytes that otherwise the individual would have difficulty absorbing. This is accomplished through a balance between the amount of carbohydrates and the amount of electrolytes in the ORC. For example, sodium absorption improves as the dextrose concentration of the oral fluid is increased up to about 2.5% w/w. But higher concentrations of dextrose increase the osmotic load in the gut, which pulls water out of the blood stream, leading to a net reduction in sodium and water absorption. This net loss of fluids and electrolytes further exacerbates dehydration.

However, only certain carbohydrates have been shown to be effective in aiding absorption of electrolytes. Generally, simple sugars such as dextrose and fructose are effective while larger carbohydrates do not provide the same benefit. Further, many Oligosaccharides are known to have limited stability in acidic medium such as is common to ORC. Because of this, conventional ORC generally do not include oligosaccharides or polysaccharides.

SUMMARY

The general inventive concepts are directed to nutritional compositions including oral rehydration compositions, and the use of nutritional compositions including oral rehydration compositions to prevent or treat dehydration. In certain exemplary embodiments, an oral rehydration composition comprising a human milk oligosaccharide is provided, In a first exemplary embodiment, a nutritional composition is provided. The nutritional composition comprises a human milk oligosaccharide selected from a fucosylated oligosaccharide, an N-acetylated oligosaccharide, and combinations thereof in an amount of about 10 mg to about 5000 mg per liter of the nutritional composition; a digestible carbohydrate in addition to the human milk oligosaccharide in an amount of from about 10 mM to about 150 mM of carbohydrate per liter of the nutritional composition; and sodium in an amount of about 10 mEq to about 100 mEq of sodium per liter of the nutritional composition.

In a second exemplary embodiment, an oral rehydration composition is provided. The oral rehydration composition comprises sodium, potassium, chloride, a digestible carbohydrate, an indigestible carbohydrate, and a human milk oligosaccharide in an amount of about 10 mg to about 5000 mg per liter of the oral rehydration composition.

In a third exemplary embodiment, an acidic, thermally-treated nutritional liquid is provided. The nutritional liquid comprises at least one of 2'-fucosyllactose and lacto-N-neotetraose in an amount of from about 10 mg to about 5000 mg per liter of the nutritional liquid.

In a fourth exemplary embodiment, an oral rehydration composition is provided. The oral rehydration composition comprises sodium, potassium, chloride, a digestible carbohydrate, and at least one human milk oligosaccharide selected from a fucosylated oligosaccharide and a N-acetylated oligosaccharide.

DETAILED DESCRIPTION

The general inventive concepts are directed to nutritional compositions including ORC, and the use of nutritional compositions to prevent or treat dehydration. In certain embodiments, the ORC has an acidic pH, and comprises a digestible carbohydrate, sodium, and an oligosaccharide. Compositions according to the exemplary embodiments may be useful for at least one of: rehydration, promoting faster recovery from diarrheal illness, reducing intestinal spasms due to diarrhea, reducing the duration of diarrhea, reducing vomiting and nausea, and promoting faster re-colonization of the gastrointestinal (GI) tract by beneficial flora following antibiotic treatment.

The term "individual" as used herein, unless otherwise specified, refers to a mammal. In certain exemplary embodiments, the individual is a human, including an infant, a child and an adult.

The term "infant" as used herein, unless otherwise specified, refers to children not more than about one year of age, and includes infants from 0 to about 4 months of age, infants from about 4 to about 8 months of age, infants from about 8 to about 12 months of age, low birth weight infants at less than 2,500 grams at birth, and preterm infants born at less than about 37 weeks gestational age, typically from about 26 weeks to about 34 weeks gestational age. The term "child" or "children" as used herein refers to children not more than 12 years of age, and includes children from about 12 months to about 12 years of age. The term "adult" as used herein refers to adults and children about 12 years of age and older.

One "milliequivalent" (mEq) refers to the number of ions in solution as determined by their concentration in a given volume. This measure is expressed as the number of milliequivalents per liter (mEq/L). Milliequivalents may be converted to milligrams by multiplying mEq by the atomic weight of the mineral and then dividing that number by the valence of the mineral.

The terms "administer," "administering," "administered," or "administration" as used herein, unless otherwise specified, should be understood to include providing the nutritional composition to an individual, the act of consuming the nutritional composition, and combinations thereof. In addition, it should be understood that the methods of administering disclosed herein may be practiced with or without doctor supervision or other medical direction.

The terms "human milk oligosaccharide" or "HMO," unless otherwise specified, refers generally to a number of complex carbohydrates found in human breast milk that can be in acidic or neutral form. Exemplary non-limiting human milk oligosaccharides include, 2'-fucosyllactose, 3'-fucosyllactose, lacto-N-neotetraose, and lacto-N-tetraose.

The term "shelf stable" as used herein, unless otherwise specified, refers to a nutritional product that remains commercially stable after being packaged and then stored at 18-24° C. for at least 3 months, including from about 6 months to about 24 months, and also including from about 12 months to about 18 months.

The exemplary nutritional compositions disclosed herein, and utilized in the exemplary methods, include those suitable for oral administration. Oral administration, as defined herein, includes any form of administration in which the nutritional compositions passes through the esophagus of the individual. For example, oral administration includes nasogastric intubation, in which a tube is run through the nose to the stomach of the individual to administer food or drugs.

All percentages, parts and ratios as used herein, are by weight of the total composition, unless otherwise specified. All such weights as they pertain to listed ingredients are based on the active level and, therefore, do not include solvents or by-products that may be included in commercially available materials, unless otherwise specified.

Any reference in the specification or claims to a quantity of an electrolyte should be construed as referring to the final concentration of the electrolyte in the nutritional composition. Tap water often contains residual sodium, chlorine, etc. A value of 15 mEq of sodium in this application means that the total sodium present in the nutritional composition equals 15 mEq, taking into account both added sodium as well as the sodium present in the water used to manufacture the nutritional composition. This holds true for all electrolytes.

All references to singular characteristics or limitations of the present disclosure shall include the corresponding plural characteristic or limitation, and vice versa, unless otherwise specified or clearly implied to the contrary by the context in which the reference is made.

The nutritional compositions of the present disclosure may also be substantially free of any optional ingredient or feature described herein, provided that the remaining formula still contains all of the required ingredients or features as described herein. In this context, and unless otherwise specified, the term "substantially free" means that the selected composition contains less than a functional amount of the optional ingredient, typically less than 0.1% by weight, and also including zero percent by weight of such optional or selected essential ingredient.

In certain exemplary embodiments, the nutritional composition, such as an ORC, is formulated as a clear liquid (i.e., a solution) having an acidic pH. In certain exemplary embodiments, the nutritional composition is an aqueous composition and has a pH ranging from 2 to 6.5. In certain exemplary embodiments, the pH of the nutritional composition is about 2.5 to about 4.6. In certain exemplary embodiments, the pH of the nutritional composition is about 2.5 to about 3.5.

Typically, the nutritional composition is desired to be clear, or at least substantially translucent, and is substantially free of fat. As used herein "substantially free of fat" refers to a nutritional composition containing less than 0.5%, including less than 0.1%, fat by weight of the total composition. "Substantially free of fat" also may refer to a nutritional composition disclosed herein that contains no fat, i.e., zero fat. In those embodiments of the nutritional composition that are substantially free of fat but have some amount of fat present, the fat may be present as a result of being inherently present in another ingredient, or the fat may be present as a result of being added as one or more separate sources of fat. In certain exemplary embodiments, the term substantially free of fat refers to a nutritional composition wherein there is no caloric lipid component (i.e., less than a functional amount of the ingredient, typically less than 0.5% by weight, and also including zero percent by weight, of such ingredient) in the nutritional composition. In certain exemplary embodiments, a nutritional composition that includes a lipid that is introduced as a component of one or more ingredients but does not contribute substantially to the caloric value of the nutritional composition, is considered to be substantially free of fat. In certain exemplary embodiments, a nutritional composition that includes emulsifiers, phospholipids or the like, in amounts that do not contribute substantially to the caloric value of the nutritional composition, is considered to be substantially free of fat.

The nutritional composition and corresponding manufacturing methods disclosed herein can comprise, consist of or consist essentially of the essential elements and limitations of the disclosure as described herein, as well as any additional or optional ingredients, components, or limitations described herein or otherwise useful in oral rehydration applications.

Oral Rehydration Therapy (ORT) typically involves the administration of a nutritional composition containing, at a minimum, a digestible carbohydrate (often dextrose) and sodium in water. A nutritional composition such as this provides rapid, effective hydration because sodium ion absorption in the intestines causes water molecules associated with the sodium ion to also be absorbed. This sodium absorption is activated by dextrose. Specifically, dextrose that crosses the intestinal epithelium brings sodium ions, raising the concentration of sodium ions in the blood stream and pulling water out of the gut.

A nutritional composition can thus be used to correct the fluid and electrolyte losses associated with acute infectious diarrhea or vomiting, or both, to treat hyponatremia or hypohydration due to exercise, changes in altitude, or fever, and to maintain a healthy level of hydration. The general inventive concepts are directed to an nutritional composition comprising sodium, a digestible carbohydrate, and an oligosaccharide (in particular fucosylated oligosaccharides and N-acetylated oligosaccharides), in particular, an oligosaccharide that is stable in an acidic environment. The general inventive concepts also relate to the use of the nutritional compositions for the prevention/treatment of dehydration due to fever and/or other medical conditions not associated with diarrhea and vomiting.

Inclusion of certain oligosaccharides in ORT is complicated by the fact that many are unstable in acidic medium (many forms of ORT are acidic), especially when stored for extended (i.e., more than 3 months) periods of time. When subjected to acidic medium, the bonds between the sugars that make up the oligosaccharide are hydrolyzed giving off the individual sugars. Nevertheless, provided herein are nutritional compositions (including acidic nutritional compositions such as ORC) comprising oligosaccharides, including HMOs, which demonstrate enhanced shelf stability.

Prebiotics are generally defined as non-digestible food ingredients that beneficially affect the host by stimulating the growth or activity, or both, of beneficial bacteria in the colon. These bacteria have been shown to provide benefits for digestion and boost immune function. In this regard they may provide benefits to those experiencing dehydration. Oligosaccharides are short to medium chain polymers of simple carbohydrates (i.e., sugars), and many have demonstrated prebiotic activity. Examples of oligosaccharides include galactooligosaccharide (GOS) 2'-fucosyllactose (2'-FL) and lacto-N-neotetraose (LNnT).

Human milk is known to contain more than 100 different oligosaccharides. Many beneficial functions have been attributed to HMOs. Certain HMOs have been shown to be beneficial biologically. For this reason, the supplementation nutritional compositions with human milk oligosaccharides is desirable. The nutritional compositions according to the general inventive concepts include at least one HMO, and in certain embodiments, a combination of two or more HMOs.

The HMO may be included in the nutritional compositions alone, or in some embodiments, in combination with other components (e.g., prebiotic oligosaccharides, probiotics, etc.) as described herein. In many embodiments, HMOs are included in the nutritional compositions with multiple additional components. The HMO may be isolated or enriched from milk(s) secreted by mammals including, but not limited to: human, bovine, ovine, porcine, or caprine species. The HMO may also be produced via microbial fermentation, enzymatic processes, chemical synthesis, or combinations thereof.

Suitable HMOs for use in the nutritional compositions may generally include neutral oligosaccharides, acidic oligosaccharides, and more particularly include fucosylated oligosaccharides and N-acetylated oligosaccharides. Specific non-limiting examples of HMOs that may be included individually or in combination in the exemplary nutritional compositions include: 2'-FL; 3'-Fucosyllactose (3'-FL); Lacto-N-tetraose (LNT); and LNnT.

Optional HMOs that may be included in certain exemplary embodiments include sialic acid (i.e., free sialic acid, lipid-bound sialic acid, protein-bound sialic acid); D-glucose (Glc); D-galactose (Gal); N-acetylglucosamine (GlcNAc); L-fucose (L-Fuc); D-fucose (D-fuc); fucosyl otigosaccharides (i.e., Lacto-N-fucopentaose I; Lacto-N-fucopentaose Lacto-N-fucopentaose In; Lacto-N-difucohexaose I; and Lactodifucotetraose); non-fucosylated, non-sialylated oligosaccharides (i.e.); sialyloligosaccharides (i.e., 3'-Sialyl-3-fucosyllactose; Disialomonofucosyllacto-N-neohexaose; Monofucosylmonosialyllacto-N-octaose (sialyl Lea); Sialyllacto-N-fucohexaose II; Disialyllacto-N-fucopentaose II; Monofucosyldisialyliacto-N-tetraose); and sialyl fucosyl oligosaccharides i.e., 2'-Sialyllactose; 2-Sialyllactosamine; 3'-Sialyllactose; 3'-Sialyllactosamine; 6'-Sialyllactose; 6'-Sialyllactosamine; Sialyllacto-N-neotetraose c; Monosialyllacto-N-hexaose; Disialyllacto-N-hexaose I; Monosialyllacto-N-neohexaose I; Monosialyl-lacto-N-neohexaose II; Disialyllacto-N-neohexaose; Disiatyllacto-N-tetraose; Disiatyllacto-N-hexaose II; Sialyl-lacto-N-tetraose a; Disialyllacto-N-hexaose I; and Sialyl-lacto-N-tetraose. Other suitable examples of HMOs that may be included in the compositions of the present disclosure include tacto-N-fucopentaose V, tacto-N-hexaose, para-lacto-N-hexaose, lacto-N-neohexaose, para-lacto-N-neohexaose, monofucosyllacto-N-hexaose IL isomeric fucosylated lacto-N-hexaose (1), isomeric fucosylated lacto-N-hexaose (3), isomeric fucosylated lacto-N-hexaose (2), difucosyl-para-lacto-N-neohexaose, difucosyl-para-lacto-N-hexaose, difucosyllacto-N-hexaose, lacto-N-neooctaose, para-lacto-N-octanose, iso-tacto-N-octaose, lacto-N-octaose, monofucosyllacto-neooctaose, monofucosyllacto-N-octaose, difucosyllacto-N-octaose I, difucosyllacto-N-octaose difucosyllacto-N-neoocataose difucosyllacto-N-neoocataose lacto-N-decaose, trifucosyllacto-N-neooctaose, trifucosyllacto-N-octaose, trifucosyl-iso-Lacto-N-octaose, lacto-N-difuco-hexaose sialyl-lacto-N-tetraose a, sialyllacto-N-tetraose b, sialyl-lacto-N-tetraose c, sialyl-fucosyllacto-N-tetraose I, sialyl-fucosyl-lacto-N-tetraose II, and disialyl-lacto-N-tetraose, and combinations thereof. Due to acid stability, certain sialylated oligosaccharides (e.g., 6'-sialyllactose) and fructooligosaccharides (FOS) may be less preferred, but may still be included in certain exemplary embodiments in accordance with the exemplary embodiments discussed below.

Particularly suitable nutritional compositions include at least one of the following HMOs: fucosylated oligosaccharides and N-acetylated oligosaccharides. Specific non-limiting examples of HMOs that are particularly suited for inclusion individually or in combination in the exemplary nutritional compositions include: 2'-FL, 3'-FL, LNT, and LNnT.

2'-FL is a soluble milk glycan present in human milk. 2'-FL has been shown to be beneficial for the reduction of inflammation, fighting infections, regulation of gastrointestinal contractions, promotion of intestinal differentiation, as well as general prebiotic properties. Many known ORTs do not properly address the recovery of intestinal epithelium or the re-colonization of beneficial gut flora. Provided herein are nutritional compositions and oral rehydration compositions that address these unmet needs via the novel inclusion of oligosaccharides. In certain exemplary embodiments, the nutritional compositions address these needs via the inclusion of shelf-stable HMOs such as 2'-FL.

In certain exemplary embodiments, the nutritional compositions comprise a human milk oligosaccharide selected from a fucosylated oligosaccharide and an N-acetylated oligosaccharide in an amount of about 10 mg to about 5000 mg per liter of the nutritional composition. In certain exemplary embodiments, the human milk oligosaccharide is selected from 2'-fucosyllactose and lacto-N-neotetraose. In certain exemplary embodiments, the nutritional composition comprises 2'-fucosyllactose in an amount of about 20 mg to about 4000 mg per liter of the nutritional composition.

In addition to 2'-FL, other oligosaccharides may provide similar benefits. In certain exemplary embodiments, the nutritional composition further comprises a neutral human milk oligosaccharide. Other human milk oligosaccharides suitable for inclusion in the exemplary embodiments include fucosylated oligosaccharides and N-acetylated oligosaccharides, and in particular 3'-fucosyllactose, LNT, and LNnT. In certain exemplary embodiments, the neutral human milk oligosaccharide is present in an amount of about 10 mg to about 5000 mg per liter of the nutritional composition.

In certain embodiments, the nutritional compositions may also include an oligosaccharide (also referred to as an indigestible carbohydrate) or a source of an oligosaccharide selected from GOS and xylooligosaccharides (XOS). In certain exemplary embodiments, the nutritional compositions comprise an indigestible oligosaccharide or a source of indigestible oligosaccharide. In certain exemplary embodiments, the nutritional compositions comprise GOS. GOS, also known as oligogalactosyllactose, oligogalactose, oligolactose, or transgalactooligosaccharides, is a known prebiotic oligosaccharide. GOS is a polymer of lactose (a disaccharide itself), and most sources of GOS comprise some inherent free lactose. This inherent lactose poses a problem for use of GOS in a nutritional composition intended for use to treat the symptoms of dehydration. Lactose is known to exacerbate the symptoms of, for example, diarrhea, and thus ingredients that include lactose are, as a rule, generally not included in dehydration/rehydration therapies. Additional non-limiting examples of indigestible carbohydrates include oligofructose, inulin, polydextrose, hydrolyzed pectin, and gums.

In certain exemplary embodiments, the nutritional compositions comprise a digestible carbohydrate (or simply a carbohydrate) or a source of digestible carbohydrate, in addition to the oligosaccharides. The quantity of digestible carbohydrate present in the nutritional compositions can vary depending upon the needs of the ultimate user. In certain exemplary embodiments, the nutritional composition comprises a digestible carbohydrate in an amount of about 10 mM to about 150 mM of carbohydrate in the nutritional composition. In certain exemplary embodiments, the nutritional composition comprises a digestible carbohydrate in an amount of about 50 mM to about 150 mM of carbohydrate in the nutritional composition. Non-limiting examples of carbohydrates suitable for use in the exemplary embodiments include dextrose, maltodextrin, starch, isomaltulose, sucromalt, rice syrup, and rice syrup solids. In certain exemplary embodiments, the digestible carbohydrate comprises dextrose.

The amount of dextrose present in exemplary embodiments of the nutritional composition may also be expressed in an amount of dextrose in grams per liter. In certain exemplary embodiments, dextrose is included in the nutritional composition in an amount from about 1.8 g/L to about 60 g/L of the nutritional composition. In certain exemplary embodiments, dextrose is present in an amount from about 4.5 g/L to about 60 g/L. In certain exemplary embodiments, dextrose is present in an amount from about 5 g/L to about 60 g/L. In certain exemplary embodiments, dextrose is present in an amount from about 10 to about 10 g/L. In certain exemplary embodiments, dextrose is present in an amount from about 5 g/L to about 30 g/L. In certain exemplary embodiments, dextrose is present in an amount from about 10 to about 25 g/L.

In certain exemplary embodiments, the nutritional composition may also optionally include a source of digestible carbohydrate other than dextrose. The carbohydrates may be simple and/or complex carbohydrates, including monosaccharides, disaccharides, oligosaccharides, and polysaccharides. Specific examples of suitable carbohydrates include, but are not limited to sucrose, fructose, dextrose polymers, corn syrup, high fructose corn syrup, sucrose, lactose, maltose, amylose, glycogen, galactose, allose, altrose, mannose, gulose, idose, talose, ribose, arabinose, lyxose, ribose, xylose, erythrose, threose, and combinations thereof.

In certain exemplary embodiments, the nutritional composition comprises sodium. The sodium in the nutritional compositions may be present as a cation of a salt. Examples of suitable sodium sources include sodium chloride, sodium phosphate, sodium citrate, sodium carbonate, sodium bicarbonate, sodium hydroxide, sodium ascorbate, and combinations thereof.

The quantity of sodium ions present in the nutritional composition varies widely and the ultimate amount may depend on the needs of the particular user. In certain exemplary embodiments, sodium is present in the nutritional composition in an amount of about 10 mEq/L to about 100 mEq/L of the nutritional composition. In certain exemplary embodiments, sodium is present in the nutritional composition in an amount of about 10 mEq/L to about 95 mEq/L of the nutritional composition. In certain exemplary embodiments, a sodium is present in an amount sufficient to provide from about 15 mEq/L to about 95 mEq/L. In certain exemplary embodiments, a sodium is present in an amount sufficient to provide from about 25 mEq/L to about 95 mEq/L. In certain exemplary embodiments, sodium is present in an amount sufficient to provide from about 30 mEq/L to about 95 mEq/L. In certain exemplary embodiments, sodium is present in the nutritional composition in an amount of about 10 mEq/L, to about 90 mEq/L of the nutritional composition. In certain exemplary embodiments, sodium is present in an amount sufficient to provide from about 45 mEq/L to about 90 mEq/L of the nutritional composition. In certain exemplary embodiments, sodium is present in an amount sufficient to provide from about 15 mEq/L to about 60 mEq/L of the nutritional composition. In certain exemplary embodiments, sodium is present in an amount sufficient to provide from about 45 mEq/L to about 60 mEq/L of the nutritional composition.

In addition to the oligosaccharides, dextrose, and sodium, the nutritional compositions according to certain exemplary embodiments may contain all the necessary electrolytes and levels thereof required b the Food and Drug Administration for oral rehydration formulations sold in the United States or recommended by the World Health Organization for use globally.

In certain exemplary embodiments, the nutritional composition further comprises citrate or a source of citrate. The quantity of citrate present in the nutritional composition varies widely and the ultimate amount may vary depending on the needs of the particular user. Examples of suitable forms of citrate for inclusion in the exemplary embodiments include potassium citrate, sodium citrate and zinc citrate.

In certain exemplary embodiments, the nutritional composition comprises citrate in an amount sufficient to provide from about 1 mEq/L to about 200 mEq/L of the nutritional composition. In certain exemplary embodiments, the nutritional composition comprises citrate in an amount sufficient to provide from about 1 mEq/L to about 180 mEq/L of the nutritional composition. In certain exemplary embodiments, the nutritional composition comprises citrate in an amount sufficient to provide from about 1 mEq/L to about 160 mEq/L of the nutritional composition. In certain exemplary embodiments, the nutritional composition comprises citrate in an amount sufficient to provide from about 1 mEq/L to about 140 mEq/L of the nutritional composition. In certain exemplary embodiments, the nutritional composition comprises citrate in an amount sufficient to provide from about 1 mEq/L to about 130 mEq/L of the nutritional composition. In certain exemplary embodiments, the nutritional composition comprises citrate in an amount sufficient to provide from about 3 mEq/L to about 200 mEq/L of the nutritional composition. In certain exemplary embodiments, citrate is present in an amount sufficient to provide from about 3 mEq/L to about 125 mEq/L of the nutritional composition. In certain exemplary embodiments, citrate is present in an amount sufficient to provide from about 3 mEq/L to about 100 mEq/L of the nutritional composition. In certain exemplary embodiments, citrate is present in an amount sufficient to provide from about 3 mEq/L to about 90 mEq/L of the nutritional composition. In certain exemplary embodiments, citrate is present in an amount sufficient to provide from about 3 mEq/L to about 75 mEq/L of the nutritional composition. In certain exemplary embodiments, citrate is present in an amount sufficient to provide from about 5 mEq/L to about 125 mEq/L of the nutritional composition. In certain exemplary embodiments, citrate is present in an amount sufficient to provide from about 8 mEq/L to about 125 mEq/L of the nutritional composition. In certain exemplary embodiments, citrate is present in an amount sufficient to provide from about 8 mEq/L to about 100 mEq/L of the nutritional composition. In certain exemplary embodiments, citrate is present in an amount sufficient to provide from about 8 mEq/L to about 50 mEq/L of the nutritional composition. These amounts include citrates from any source, including citric acid; citric ester that can be hydrolyzed into citric acid or a citrate ion; or a citrate salt, such as potassium citrate, sodium citrate, zinc citrate, and combinations thereof.

In certain exemplary embodiments, the nutritional composition comprises chloride or a source of chloride. The chloride in an nutritional composition may be present as an ion in the liquid, and may be in equilibrium with a salt. Examples of suitable chloride salts include, but are not limited to sodium chloride, potassium chloride, calcium chloride, magnesium chloride, and combinations thereof. The amount of chloride present in the nutritional composition may vary widely and the ultimate amount may vary depending on the needs of the particular user. In certain exemplary embodiments, the nutritional composition comprises chloride in an amount from about 5 mEq/L to about 90 mEq/L of the nutritional composition. In certain exemplary embodiments, the nutritional composition comprises chloride in an amount from about 10 mEq/L to about 85 mEq/L of the nutritional composition. In certain exemplary embodiments, the nutritional composition comprises chloride in an amount from about 20 mEq/L to about 90 mEq/L of the nutritional composition. In certain exemplary embodiments, the nutritional composition comprises chloride in an amount from about 20 mEq/L to about 85 mEq/L of the nutritional composition. In certain exemplary embodiments, the nutritional composition comprises chloride in an amount from about 20 mEq/L to about 80 mEq/L of the nutritional composition. In certain exemplary embodiments, the nutritional composition comprises chloride in an amount from about 15 mEq/L to about 80 mEq/L of the nutritional composition.

In certain exemplary embodiments, the nutritional composition may further comprise zinc or a source of zinc. The source of zinc is generally not critical. Any zinc salt suitable for human consumption may be used in the nutritional composition. Examples of suitable zinc sources include zinc gluconate, zinc sulfate, zinc chloride, zinc citrate, zinc bicarbonate, zinc carbonate, zinc hydroxide, zinc lactate, zinc acetate, zinc fluoride, zinc bromide, zinc sulfonate, and combinations thereof. The amount of zinc used in the nutritional composition can vary widely and the ultimate amount may vary depending on the needs of the particular user. In certain exemplary embodiments, zinc is present in the nutritional composition in an amount from about 0.1 mEq/L to about 95 mEq/L of the nutritional composition.

In certain exemplary embodiments, the nutritional composition may further comprise potassium or a source of potassium ions. The potassium in a nutritional composition may be present as an ion in the liquid, and may be in equilibrium with a salt. Examples of potassium salts include potassium chloride, potassium phosphate, potassium citrate, potassium carbonate, potassium bicarbonate, potassium hydroxide, and combinations thereof. The quantity of potassium present in the nutritional composition can vary widely and the ultimate amount may vary depending on the needs of the particular user. In certain exemplary embodiments, potassium is present in an amount sufficient to provide from about 3 mEq/L to about 1.00 mEq/L of the nutritional composition. In certain exemplary embodiments, potassium is present in an amount sufficient to provide from about 5 mEq/L to about 100 mEq/L of the nutritional composition. In certain exemplary embodiments, potassium is present in an amount sufficient to provide from about 3 mEq/L to about 50 mEq/L of the nutritional composition. In certain exemplary embodiments, potassium is present in an amount sufficient to provide from about 10 mEq/L to about 50 mEq/L of the nutritional composition. In certain exemplary embodiments, potassium is present in an amount sufficient to provide from about 3 mEq/L to about 25 mEq/L of the nutritional composition. In certain exemplary embodiments, a source of potassium is present in an amount sufficient to provide from about 15 mEq/L to about 25 mEq/L of the nutritional composition.

In certain exemplary embodiments, calcium or a calcium containing substance may also be included in the nutritional composition. Examples of suitable calcium containing substances include calcium chloride, calcium oxide, calcium hydroxide, calcium carbonate, calcium orthophosphate (including mono-, di- and tricalcium phosphate), calcium lactate, calcium gluconate, calcium citrate, calcium acetate, calcium ascorbate, calcium tartarate, calcium malate and mixtures of these. The quantity of calcium present in the nutritional composition can vary widely and the ultimate amount may vary depending on the needs of the particular user. In certain exemplary embodiments, calcium is present in an amount sufficient to provide from about 0.25 mEq/L to about 30 mEq/L the nutritional composition. In certain exemplary embodiments, calcium is present in an amount sufficient to provide from about 0.25 mEq/L to about 20 mEq/L the nutritional composition. In certain exemplary embodiments, calcium is present in an amount sufficient to provide from about 0.4 mEq/L to about 20 mEq/L the nutritional composition. In certain exemplary embodiments, calcium is present in an amount sufficient to provide from about 15 mEq/L to about 20 mEq/L the nutritional composition.

In certain exemplary embodiments, the nutritional composition comprises at least one of protein and fat.

In certain exemplary embodiments, the nutritional composition comprises protein from one or more sources. Suitable sources of protein or sources thereof include, but are not limited to, animal products (e.g., dairy proteins, meat, fish, egg albumen), cereals (e.g., rice, corn), vegetables (e.g., soy, pea, potato), and combinations thereof. Additional protein sources can also include, peptides and free amino acids known for use in nutritional compositions, non-limiting examples of which include L-tryptophan, L-glutamine, L-tyrosine, L-methionine, L-cysteine, L-arginine, L-threonine, L-serine, and combinations thereof.

In certain exemplary embodiments, the nutritional composition comprises fat from one or more sources. Suitable sources of fat or sources thereof include, but are not limited to, coconut oil, fractionated coconut oil, soy oil, corn oil, olive oil, safflower oil, high oleic safflower oil, MCT (medium chain triglycerides) oil, sunflower oil, high oleic sunflower oil, palm and palm kernel oils, palm olein, canola oil, marine oils, cottonseed oils, non-dairy creamer, and combinations thereof.

In certain exemplary embodiments, the nutritional composition further comprises a probiotic. In certain exemplary embodiments, the probiotic is selected from the group of *B. animalis* spp *lactis* BB-12, *B. infantis* ATCC15697, *B. infantis* M-63, *B. Infantis* 35624, *B. lactis* HNO19, *B. lactis* Bi07, *L. rhamnosus* LGG, *L. rhamnosus* HN001, *L. acidophilus* LA-5, *L. acidpohilus* NCFM, *L. fermentum* CECT5716, *B. longum* BB536, *B. longum* AH1205, *B. breve* M-16V, *L. reuteri* ATCC 55730, *L. reuteri* ATCC PTA-6475, *L. reuteri* DSM 17938, and combinations thereof.

In certain exemplary embodiments, the nutritional composition includes one or more additional ingredients. Examples of additional ingredients for inclusion in the exemplary embodiments include postbiotics (metabolites of prebiotics) tong chain polyunusaturated fatty acids (DHA, ARA, DPA, EPA, etc.), nucleotides, antioxidant/anti-inflammatory compounds such as tocopherols; carotenoids; ascorbate/vitamin C; ascorbyl palmitate; polyphenols; glutathione; and superoxide dismutase, bioactive factors (e.g., growth hormones, cytokines, antibodies, and immunoglobulins), of human or bovine origin, tributyrin or other SCFA-containing mono-, di-, or triglycerides, human milk derived lipids, free amino acids or peptides (e.g., HMB, arginine, leucine, and glutathione), lactose, other water- and fat-soluble vitamins, minerals and trace elements. Further examples of additional ingredients that may be used in exemplary embodiments include flavorants, colorants, preservatives, excipients, gelling agents, amino acids, calcium, vitamins, dietary supplements, and combinations thereof. In general, the amount of any additional ingredients in an nutritional composition is such that the primary ingredients remain within the desired ranges.

In certain exemplary embodiments, a flavorant may be present to add or modify a flavor in the nutritional composition, or to enhance its palatability, especially in a pediatric population. Examples of suitable flavorants include anise oil, cinnamon oil, vanilla, vanillin, cocoa, chocolate, menthol, grape, fruit punch flavoring, bubble gum flavoring, peppermint oil, oil of wintergreen, clove oil, bay oil, anise oil, eucalyptus, thyme oil, cedar leaf oil, oil of nutmeg, oil of sage, oil of bitter almonds, cassia oil, citrus oils such as lemon, orange, lime and grapefruit oils, and fruit essences, including apple, pear, peach, berry, wildberry, date, blueberry, kiwi, strawberry, raspberry, cherry, plum, pineapple, and apricot.

In certain exemplary embodiments, artificial sweeteners may also be added to complement the flavor of the nutritional composition. The concentration of sweetener in the nutritional composition may be from about 0.01 to about 0.5 g/L of the nutritional composition. Useful artificial sweeteners include saccharin, nutrasweet, sucralose, aspartame, acesulfame-K (ace-K), and the like.

In certain exemplary embodiments, a colorant may be present to add or modify a color in the nutritional composition. Examples of colorants include FD&C Red No 3, FD&C Red No. 20, FD&C Yellow No, 6, FD&C Blue No. 2, D&C Green No. 5, FD&C Orange No. 5, D&C Red No. 8, caramel, ferric oxide, pigments, dyes, tints, titanium dioxide, grape skin extract, beet red powder, beta carotene, annato, carmine, turmeric, paprika, and the like.

In certain exemplary embodiments, a preservative may be present to provide a longer shelf life to a pre-packaged nutritional composition, or to extend the potability lifetime of a nutritional composition. Examples of suitable preservatives include, but are not limited to, potassium sorbate and sodium benzoate.

In certain exemplary embodiments, a gelling agent may be present in the nutritional composition, such that the nutritional composition can be turned into a gel, such as a flowable gel or a self-supporting gel. Nutritional composition gels may provide improved patient compliance in consuming a nutritional composition, especially in a pediatric population. Gelled rehydration formulas are described in U.S. Pat. No. 6,572,898, hereby incorporated by reference herein. Gelling agents may be included in the nutritional composition in amounts of from about 0.05 to about 50% (w/w).

The nutritional composition according to certain exemplary embodiments can be manufactured using techniques well known to those skilled in the art. For instance, the nutritional composition may be prepared by combining the non-aqueous "dry") ingredients of the nutritional composition, for example by dry blending, and dispersing the dry ingredients in a suitable amount of water to provide a liquid having the appropriate concentrations of ingredients, as set forth herein. Alternately, one or more of the dry ingredients may be added separately to the water. The nutritional composition may optionally be heated to the appropriate temperature to dissolve all the ingredients, filtered, packaged, and sterilized (sterilization may include heating, pasteurization, radiation, an aseptic process, etc.) sterilization to food grade standards as is known in the art.

The nutritional composition according to certain exemplary embodiments may generally be heat sterilized either by a retort process, an aseptic process, or a hot fill process.

A typical retort process involves introducing the nutritional composition into a metal or plastic container, sealing the container, and then heating the sealed container for a time period and to a temperature sufficient for sterilization. Aseptic sterilization involves separately sterilizing a metal or plastic container and the nutritional composition, and then combining the sterilized container and the nutritional composition in a clean room environment and sealing the container. In a hot fill process, the container is filled with the nutritional composition and sealed at product temperatures above room temperature.

More specifically, in an exemplary retort sterilization method, the nutritional composition is usually preheated and then filled into a clean can, hermetically sealed, and placed in a steam chamber and sterilized, at a temperature of about 100° C., or in certain embodiments about 121° C. for about 15 to about 45 minutes. The batch is then cooled and the retort filled with a new batch. Because sterilization takes place after filling, the need for aseptic handling is eliminated, although heat resistant plastic (or another heat resistant material) must be used due to the high temperatures involved. In one specific retort sterilization embodiment, a hydrostatic tower method is utilized and includes conveying slowly the sealed containers through successive heating and cooling zones in a sterilizer. The zones are dimensioned to correspond to the required temperatures and holding times in the various treatment stages.

In certain exemplary embodiments according to the aseptic sterilization method, the nutritional composition is sterilized and a container is separately sterilized. The nutritional composition may be sterilized utilizing a heating process, for example. The container may be sterilized by spraying the interior wall of the container with hydrogen peroxide and then drying the interior wall. Once the container and the nutritional composition have both been sterilized, the nutritional composition is introduced into the container in a clean room environment and the container sealed.

In certain exemplary embodiments, a hot fill processes alone can be used to sterilize a high acid product (approximately below pH 4.6). In hot fill sterilization, the container is filled with the nutritional composition and the container is sealed at approximately 180° F. The filled container is then rotated end-over-end so that the hot nutritional composition contacts all surfaces and, finally, it is held hot for approximately five to ten minutes to kill all viable microorganisms. Microorganisms which are viable at low pH are molds and yeasts. If the product is a low acid product, approximately above pH 4.6, the hot fill process does not produce adequate sterility. Terminal sterilization is used to kill harmful organisms potentially viable above 4.6. Terminal sterilization kills potentially viable organisms by raising product and container temperatures to the equivalent of 250° F. for a time equivalent to at least 3 minutes, more often, in excess of 10 minutes as determined using established practices to calculate sterilization process time as a function of product temperature history. The length of time the product and container are held at an elevated temperature can be reduced markedly by using sterilizer and product temperatures in excess of 250° F. Sterilizer and product temperatures well in excess of 250° F. are commonly used to reduce sterilization process time.

In certain exemplary embodiments, a nutritional composition may be packaged in a container such as a glass or plastic bottle, a plastic pouch, or a paper-based carton. In certain exemplary embodiments, a nutritional composition may be formed by combining water with the remaining nutritional composition ingredients, agitating and/or heating the mixture to dissolve the ingredients, and then packaging the nutritional composition in a container. The nutritional composition may be sterilized before or after being packaged, such as by retort, aseptic, or hot fill sterilization, as discussed above. The nutritional composition may be packaged in a container that includes an oxygen barrier, an oxygen scavenger, and/or an ultraviolet radiation barrier. A single package of nutritional composition may contain a single serving, such as 12 fl.oz. (0.35 L) or 1 L. A single package of nutritional composition may contain multiple servings, such as multiples of 12 fl.oz. (0.35 L) or of 1 L.

In certain exemplary embodiments, a nutritional composition may also be packaged in non-liquid forms, provided the nutritional composition has undergone heat sterilization. In certain exemplary embodiments, a nutritional composition may be packaged as a gel containing one or more gelling agents as described above. In certain exemplary embodiments, a nutritional composition may be packaged as a frozen solution. Frozen nutritional compositions may be in the form of ice cubes, ice on a stick (i.e., "freezer pop"), crushed ice, or shaved ice, for example. Advantageously, frozen nutritional composition may provide improved patient compliance, particularly in pediatric populations. Frozen nutritional compositions are disclosed, for example, in U.S. Pat. No. 5,869,459, hereby incorporated by reference herein.

Nutritional compositions according to the exemplary embodiments may be administered in a variety of different forms, depending upon patient preference. For example, some children will consume a nutritional composition more readily if it is frozen, like a freezer pop. The nutritional composition may be administered as a frozen nutritional composition if the patient desires such a choice. Other examples of suitable product forms are set forth herein, such as powders and gels.

In certain exemplary embodiments, the nutritional composition is an oral rehydration composition in the form of a gel or frozen pop comprising sodium, potassium, chloride, a digestible carbohydrate, and at least one human milk oligosaccharide selected from a fucosylated oligosaccharide and a N-acetylated oligosaccharide present in an amount of about 10 mg to about 5000 mg per liter of the oral rehydration composition.

In certain exemplary embodiments, the nutritional composition is an oral rehydration composition in the form of a reconstitutable powder and the at least one human milk oligosaccharide is present in an amount of 0.2 to 13% by weight of the powder.

In certain exemplary embodiments, the nutritional composition may be used to prevent dehydration in an individual, particularly in individuals suffering from fever. In certain embodiments, an oral rehydration formula is prepared, and orally administered to an individual at risk of developing dehydration.

The total amount of calories provided by the nutritional composition may vary widely. In certain exemplary embodiments, the nutritional composition provides from about 10 kcal/L and 200 kcal/L. In certain exemplary embodiments, the nutritional composition provides from about 30 kcal/L to about 150 kcal/L. In certain exemplary embodiments, the nutritional composition provides from about 50 kcal/L to about 100 kcal/L.

As mentioned previously, certain oligosaccharides are known to have limited stability in acidic medium. This limited stability is also known to decrease even further when subjected to heat while in an acidic medium. Because of this, oligosaccharides are not generally used in nutritional compositions with an acidic pH, such as that in most compositions intended to treat or prevent dehydration. However, provided herein are nutritional compositions including oligosaccharides, such as fucosylated oligosaccharides and N-acetylated oligosaccharides, with enhanced stability in acidic medium.

EXAMPLES

The following examples illustrate certain exemplary embodiments or features of the nutritional composition and methods encompassed by the general inventive concepts. The examples are given solely for the purpose of illustration and are not to be construed as limitations of the present disclosure, as many variations thereof are possible without departing from the spirit and scope of the general inventive concepts.

A study was conducted to determine the relative stabilities of GOS, FOS, 2'-FL, 6'-SL, and LNnT in an oral rehydration solution. A master batch of product was prepared (shown in Table 1), the pH adjusted to approx. 4.25 and subsequently divided into five sub-batches.

TABLE 1

| Ingredient | Amount per 1000 lb batch |
|---|---|
| Water | 983.4 lb |
| Dextrose | 8.5 lb |
| Potassium citrate | 1.042 kg |
| Sodium chloride | 0.970 kg |
| Sodium citrate, dihydrate | 0.511 kg |
| Citric acid, anhydrous | 1.222 kg |

Oligosaccharide ingredients were added to each of the sub-batches in amounts shown Table 2, and the pH of each sub-batch was subsequently adjusted to 3.5 with citric acid. The solutions were filled into 1 L plastic bottles, capped and retorted with a cook temperature of 217° F. for 25 minutes. Duplicate samples were collected immediately prior to sterilization and within 24 h after sterilization. Prior to sample analysis, the unsterile samples were stored at refrigerated temperature (~40° F.) and the sterilized samples were held ambient temperature.

TABLE 2

| Oligosaccharide | Target concentration in product (g/L) |
|---|---|
| GOS | 3.20 |
| FOS | 3.20 |
| 2'FL | 0.20 |
| 6'SL | 0.20 |
| LNnT | 0.256 |

Samples were analyzed by HPAEC using a Dionex ICS3000 Ion Chromatography System (Thermo Scientific, Inc., Sunnyvale, Calif.) equipped with a pulsed amperometric detector comprised of a AgCl reference electrode, gold working electrode, and CarboPac PA1 guard (4×50 mm) and analytical columns (4×250 mm). Mobile phases were degassed and pressurized with 3 to 5 psi helium, and oligosaccharides eluted from the columns using various gradients detailed in Tables 3-5 at a flow rate of 1.0 mL/min. The column and detector were held at 20±2° C. Oligosaccharide identification and concentration were determined from quadratic fit (not forced through the origin) standard curves.

Table 3 shows an exemplary chromatography gradient used for analysis of GOS, wherein Eluent 1=Laboratory Water, Eluent 2=50 mM Sodium Acetate, Eluent 3=500 mM Sodium Hydroxide, and Eluent 4=300 mM Sodium Acetate.

TABLE 3

| Time (min) | % 1 | % 2 | % 3 | % 4 |
|---|---|---|---|---|
| 0.0 | 90 | 6 | 4 | 0 |
| 26.0 | 90 | 6 | 4 | 0 |
| 26.1 | 16.7 | 0 | 0 | 83.3 |
| 29.0 | 16.7 | 0 | 0 | 83.3 |
| 29.1 | 60 | 0 | 40 | 0 |
| 32.0 | 60 | 0 | 40 | 0 |
| 32.1 | 90 | 6 | 4 | 0 |
| 46.0 | 90 | 6 | 4 | 0 |

Table 4 shows an exemplary chromatography gradient used for analysis of FOS, wherein Eluent 1=Laboratory Water, Eluent 2=Not Used, Eluent 3=500 mM Sodium Hydroxide, and Eluent 4=300 mM Sodium Acetate.

TABLE 4

| Time (min) | % 1 | % 2 | % 3 | % 4 |
|---|---|---|---|---|
| 0.0 | 80 | 0 | 20 | 0 |
| 2.0 | 80 | 0 | 20 | 0 |
| 2.1 | 76 | 0 | 20 | 4 |
| 25.0 | 48 | 0 | 20 | 32 |
| 25.1 | 0 | 0 | 20 | 80 |
| 35.1 | 0 | 0 | 20 | 80 |
| 35.2 | 80 | 0 | 20 | 0 |
| 60.0 | 80 | 0 | 20 | 0 |

Table 5 shows an exemplary chromatography gradient used for analysis of HMO's, wherein Eluent 1=Laboratory Water, Eluent 2=Not Used, Eluent 3=500 mM Sodium Hydroxide, and Eluent 4=300 mM Sodium Acetate.

TABLE 5

| Time (min) | % 1 | % 2 | % 3 | % 4 |
|---|---|---|---|---|
| 0.0 | 80 | 0 | 20 | 0 |
| 10.0 | 80 | 0 | 20 | 0 |
| 18.0 | 70 | 0 | 20 | 10 |
| 28.0 | 70 | 0 | 20 | 10 |
| 32.0 | 48 | 0 | 20 | 32 |
| 39.0 | 48 | 0 | 20 | 32 |
| 39.01 | 0 | 0 | 20 | 80 |
| 43.0 | 0 | 0 | 20 | 80 |
| 43.01 | 80 | 0 | 20 | 0 |
| 50.0 | 80 | 0 | 20 | 0 |

Table 6 shows the results of testing the sample prepared with GOS both before (unsterile) and after sterilization (sterile), as well as 3-weeks after sterilization (3-week). GOS fortification was calculated to be 3.19 g/L. Galactooligosaccharide content was based upon the determination of the enzymatically released galactose from the GOS oligomers. The samples were enzymatically treated with (3-galactosidase (pH 6.0 at 60° C. for 1 h) in order to hydrolyze the GOS oligomers to galactose and glucose (note GOS content is calculated from galactose only). Based on the results in Table 6, there appears to be minimal loss of GOS during a retort process. Additionally, there is also no loss relative to the sterilized sample 3-weeks after sterilization.

TABLE 6

| Sample | Galactose g/L | Lactose g/L | GOS g/L | % Theoretical GOS |
|---|---|---|---|---|
| Unsterile 1 | 0.0670 | 0.767 | 3.09 | 97 |
| Unsterile 2 | 0.0667 | 0.769 | 3.14 | 98.5 |
| Average | 0.0668 | 0.768 | 3.12 | 97.8 |
| Sterile 1 | 0.0679 | 0.754 | 3.08 | 96.7 |
| Sterile 2 | 0.0689 | 0.764 | 3.10 | 97.3 |
| Average | 0.0684 | 0.759 | 3.09 | 97 |
| 3-week 1 | 0.0679 | 0.0754 | 3.08 | 96.7 |
| 3-week 2 | 0.0689 | 0.0764 | 3.10 | 97.3 |
| Average | 0.0684 | 0.0759 | 3.09 | 97 |

Table 7 shows the results of testing the sample prepared with FOS both before (unsterile) and after sterilization (sterile), as well as 3-weeks after sterilization (3-week). FOS fortification was calculated to be 3.2 g/L. Testing samples were reconstituted at 10 mL to 500 mL with water, and then filtered using a 0.2 μm PES membrane syringe filter. Fructooligosaccharide content was determined from the levels of $GF_2$ (1-kestose), $GF_3$ (nystose), and $GF_4$ (1-fructofuranosyl-nystose) in commodity and product and then applying the following formula: FOS in product=$(GF_2+GF_3+GE)_{product}$ * (potency of FOS commodity/$[GF_2+GF_3+GF_4]_{commodity}$). FOS has a loss of approximately 88% during sterilization, with continued loss over 3 weeks.

TABLE 7

| Sample | GF2 g/L | GF3 g/L | GF4 g/L | FOS g/L | % Theoretical FOS |
|---|---|---|---|---|---|
| Unsterile 1 | 1.14952 | 1.4819 | 0.2680 | 3.25 | 101.6 |
| Unsterile 2 | 1.14636 | 1.4738 | 0.2664 | 3.24 | 101.2 |
| Average | 1.14794 | 1.4778 | 0.2672 | 3.24 | 101 |
| Sterile 1 | 0.19958 | 0.1220 | 0.0123 | 0.374 | 11.70 |
| Sterile 2 | 0.19907 | 0.1219 | 0.0130 | 0.375 | 11.71 |
| Average | 0.199325 | 0.12196 | 0.01264 | 0.375 | 11.7 |
| 3-week 1 | 0.18267 | 0.1156 | 0.0118 | 0.3477 | 10.87 |
| 3-week 2 | 0.18309 | 0.1144 | 0.0121 | 0.3471 | 10.85 |
| Average | 0.18288 | 0.114985 | 0.01192 | 0.347 | 10.9 |

Table 8 shows the results of testing the sample prepared with 2'-FL both before (unsterile) and after sterilization (sterile), as well as 3-weeks after sterilization (3-week). 2'-FL fortification was calculated to be 0.2 g/L. Testing samples were reconstituted at 20 mL to 100 mL with water, and then filtered using a 0.2 μm PES membrane syringe filter. 2'-FL shows a slight decrease after sterilization, however, there is no further loss observed after 3-weeks.

TABLE 8

| Sample | Lactose mg/L | Lactulose mg/L | 2'-FL mg/L | % Theoretical 2'-FL |
|---|---|---|---|---|
| Unsterile 1 | 13.94 | NAP | 200.8 | 100.4 |
| Unsterile 2 | 14.43 | NAP | 202.1 | 101.0 |
| Average | 14.2 | NAP | 201 | 101 |
| Sterile 1 | 14.5 | 3.401 | 194.8 | 97.38 |
| Sterile 2 | 14.33 | 2.617 | 196.7 | 98.35 |
| Average | 14.4 | 3.01 | 196 | 97.9 |
| 3-week 1 | 15.59 | 3.25 | 196.6 | 98.31 |
| 3-week 2 | 15.01 | 2.792 | 196.8 | 98.38 |
| Average | 15.3 | 3.02 | 197 | 98.3 |

Table 9 shows the results of testing the sample prepared with LNnT both before (unsterile) and after sterilization (sterile), as well as 3-weeks after sterilization (3-week). LNnT fortification was calculated to be 0.256 g/L. Testing samples were reconstituted at 20 mL to 100 mL with water, and then filtered using a 0.2 μm PES membrane syringe filter. As can be seen from the table, LNnT shows a no decrease after sterilization. Additionally there is no further loss of LNnT observed after 3-weeks.

TABLE 9

| Sample | Lactose mg/L | LNnT mg/L | % Theoretical LNnT |
|---|---|---|---|
| Unsterile 1 | 25.78 | 257.6 | 100.7 |
| Unsterile 2 | 25.46 | 259.4 | 101.4 |
| Average | 25.6 | 258 | 101 |
| Sterile 1 | 26.34 | 261 | 102.1 |
| Sterile 2 | 27.26 | 261.1 | 102.1 |
| Average | 26.8 | 261 | 102 |
| 3-week 1 | 28.03 | 266.5 | 104.2 |
| 3-week 2 | 28.19 | 271.0 | 106 |
| Average | 28.1 | 269 | 105 |

Table 10 shows the results of testing the sample prepared with 6'-SL both before (unsterile) and after sterilization (sterile), as well as 3-weeks after sterilization (3-week). 6'-SL fortification was calculated to be 0.2 g/L. Testing samples were reconstituted at 20 mL to 100 mL with water, and then filtered using a 0.2 μm PES membrane syringe filter. Significant loss of 6'-SL was observed upon sterilization. No additional loss of 6'-SL was observed after 3-weeks.

TABLE 10

| Sample | Lactose mg/L | Sialic Acid mg/L | 6'-SL mg/L | % Theoretical 6'-SL |
|---|---|---|---|---|
| Unsterile 1 | 24.22 | 5.055 | 170.8 | 85.42 |
| Unsterile 2 | 24.90 | 4.842 | 174.5 | 87.24 |
| Average | 24.6 | 4.95 | 173 | 86.3 |
| Sterile 1 | 149.4 | 83.46 | 10.39 | 5.195 |
| Sterile 2 | 149.4 | 83.79 | 11.0 | 5.502 |
| Average | 149 | 83.6 | 10.7 | 5.35 |
| 3-week 1 | 152.2 | 82.89 | 10.5 | 5.249 |
| 3-week 2 | 154 | 82.96 | 10.6 | 5.3 |
| Average | 153 | 82.9 | 10.5 | 5.27 |

As can be seen from the tables, GOS, 2'-FL, and LNnT demonstrated enhanced stability in the exemplary formulations, especially in comparison to the relative stability of FOS and 6'-SL. Therefore, nutritional compositions comprising fucosylated oligosaccharide, N-acetylated oligosaccharide and combinations thereof, would be expected to demonstrate shelf stability even after a heat sterilization process.

Table 11 is a listing of ingredients for a liquid nutritional composition (in the form of an ORC) having an acidic pH, a fruit flavor, and comprising a human milk oligosaccharide according to certain exemplary embodiments disclosed herein.

TABLE 11

| Ingredient | Amount per 1000 kg batch | Kg/g/mg |
|---|---|---|
| Water | Q.S. | |
| Dextrose monohydrate | 27.67 | Kg |
| Citric acid | 2.7 | Kg |
| Flavor | 2.503 | Kg |
| Potassium Citrate | 2.3 | Kg |
| Sodium Chloride | 2.140 | Kg |
| Sodium Citrate | 1.129 | Kg |
| Sucralose | 395.3 | g |
| Acesulfame Potassium | 83.99 | g |
| Zinc Gluconate | 63.70 | g |
| 2'-fucosyllactose | 20.00 | g |
| Color | 20.00 | g |

Table 12 is a listing of ingredients for a liquid nutritional composition (in the form of an ORC) having an acidic pH, a fruit flavor, and comprising a human milk oligosaccharide and an indigestible oligosaccharide according to certain exemplary embodiments disclosed herein.

TABLE 12

| Ingredient | Amount per 1000 kg batch | Kg/g/mg |
|---|---|---|
| Water | Q.S. | |
| Dextrose monohydrate | 17.9 | Kg |
| Galacto-oligosaccharides | 6.3 | Kg |
| Citric acid | 2.7 | Kg |
| Flavor | 2.5 | Kg |
| Potassium Citrate | 2.3 | Kg |
| Sodium Chloride | 2.1 | Kg |
| Sodium Citrate | 1.1 | Kg |
| Sucralose | 395.3 | g |
| Acesulfame Potassium | 84 | g |
| Zinc Gluconate | 63.7 | g |
| 2'-fucosyllactose | 20.0 | g |
| Color | 16.0 | g |

Table 13 is a listing of ingredients for a nutritional composition in the form of a frozen pop having an acidic pH, a fruit flavor, and comprising a human milk oligosaccharide and an indigestible oligosaccharide according to certain exemplary embodiments disclosed herein.

TABLE 13

| Ingredient | Amount per 1000 kg batch | Kg/g/mg |
|---|---|---|
| Water | Q.S. | |
| Dextrose | 25.5 | Kg |
| Citric acid | 5.2 | Kg |
| Sodium Chloride | 2.1 | Kg |
| Sodium Carboxy-methyl cellulose | 2.0 | Kg |
| Potassium Citrate monohydrate | 1.9 | Kg |
| Potassium sorbate | 513 | g |
| Sodium benzoate | 500 | g |
| Flavor | 500 | g |
| Sucralose | 198 | g |
| Acesulfame Potassium | 148 | g |

TABLE 13-continued

| Ingredient | Amount per 1000 kg batch | Kg/g/mg |
|---|---|---|
| 2'-fucosyllactose | 20 | g |
| Color | 11.00 | g |

Another study was performed to determine the stability of 2'-FL, LNnT, and 6'-SL in an ORC over time (e.g., 1 week, 3 weeks, 6 weeks, and 14 weeks).

Sample Preparation: A master batch with a pH of 4.25 is sub-divided. The oligosaccharides are added to the respective ORC in an amount of 0.2 g/L for 2'-FL and 6'-SL, LNnT was fortified in an amount of 0.256 g/L. The pH was then adjusted from 4.25 to 3.5 by addition of citric acid. Prior to sterilization, samples are collected to evaluate oligosaccharide levels. The formulas were then delivered into 1 L bottles and subjected to heat sterilization and allowed to cool to room temperature.

Initial Time Analysis: total solids, sodium, potassium, chloride and pH are measured and the results are shown in Table 14.

TABLE 14

| Assay | 2'-FL | 6'-SL | LNnT |
|---|---|---|---|
| Total solids | 2.04 | 1.93 | 1.94 |
| pH | 3.44 | 3.46 | 3.46 |
| Chloride mg/kg | 1330 | 1330 | 1330 |
| Potassium mg/100 g | 83.5 | 83.7 | 83.2 |
| Sodium mg/100 g | 111 | 111 | 111 |

Table 15 shows the results of sample measurements determining the levels of 2'-FL (mg/L), lactose (mg/L), and lactulose (mg/L), as determined at 0 days, 3 weeks, 6 weeks, and 14 weeks. The data on day 0 was collected in duplicate for samples prior to sterilization (unsterile) and after sterilization (sterile), thereafter the data was collected only on the sterilized samples. 2'-FL shows very little change over the course of the study. The slight fluctuation in lactose and lactulose levels are likely due to method variability.

TABLE 15

| | | 0 D | | 3 WK | | 6 WK | | 14 WK | |
|---|---|---|---|---|---|---|---|---|---|
| Assay | Sample | mg/L | % Remaining * | mg/L | % Remaining ** | mg/L | % Remaining ** | mg/L | % Remaining ** |
| 2'-FL mg/L | Unsterile 1 | 200.8 | 100.4% | NAP | NAP | NAP | NAP | NAP | NAP |
| | Unsterile 2 | 202.1 | 101% | NAP | NAP | NAP | NAP | NAP | NAP |
| | Average | 201 | 101% | NAP | NAP | NAP | NAP | NAP | NAP |
| | Sterile 1 | 194.8 | 97.38% | 196.6 | 98.31% | 197.7 | 98.83% | 201.2 | 100.6% |
| | Sterile 2 | 196.7 | 98.35% | 196.8 | 98.38% | 200.3 | 100.2% | 200.8 | 100.4% |
| | Average | 196 | 97.9% | 197 | 98.30% | 199 | 99.5% | 201 | 101% |
| Lactose mg/L | Unsterile 1 | 13.94 | NAP | NAP | NAP | NAP | NAP | NAP | NAP |
| | Unsterile 2 | 14.43 | NAP | NAP | NAP | NAP | NAP | NAP | NAP |
| | Average | 14.2 | NAP | NAP | NAP | NAP | NAP | NAP | NAP |
| | Sterile 1 | 14.5 | NAP | 15.59 | NAP | 15.35 | NAP | 15.05 | NAP |
| | Sterile 2 | 14.33 | NAP | 15.01 | NAP | 14.77 | NAP | 15.4 | NAP |
| | Average | 14.4 | NAP | 15.30 | NAP | 15.1 | NAP | 15.2 | NAP |
| Lactulose mg/L | Unsterile 1 | NAP | NAP | NAP | NAP | NAP | NAP | NAP | NAP |
| | Unsterile 2 | NAP | NAP | NAP | NAP | NAP | NAP | NAP | NAP |
| | Average | NAP | NAP | NAP | NAP | NAP | NAP | NAP | NAP |
| | Sterile 1 | 3.401 | NAP | 3.25 | NAP | 3.103 | NAP | 2.445 | NAP |
| | Sterile 2 | 2.617 | NAP | 2.792 | NAP | 2.644 | NAP | 2.937 | NAP |
| | Average | 3.01 | NAP | 3.02 | NAP | 2.870 | NAP | 2.690 | NAP |

\* % Remaining denotes the % loss or % increase for results calculated comparing the average results for unsterile to average sterile results to the target fortification. The assumed target fortification for 2'-FL is 200 mg/L.
\*\* % Remaining denotes % loss or % increase of 3, 6, and 14 weeks test results and is calculated comparing the average interval results to the average 0 D results.

Table 16 shows the results of sample measurements determining the levels of LNnT (mg/L) and % remaining, as determined at 0 days, 3 weeks, 6 weeks, and 14 weeks. The data on day 0 was collected in duplicate for samples prior to sterilization (unsterile) and after sterilization (sterile), thereafter the data was collected only on the sterilized samples. No substantial loss of LNnT was observed during the test period.

TABLE 16

| | | 0 D | | 3 WK | | 6 WK | | 14 WK | |
|---|---|---|---|---|---|---|---|---|---|
| Assay | Sample | mg/L | % Remaining * | mg/L | % Remaining ** | mg/L | % Remaining ** | mg/L | % Remaining ** |
| LNnT mg/L | Unsterile 1 | 257.6 | 100.7% | NAP | NAP | NAP | NAP | NAP | NAP |
| | Unsterile 2 | 259.4 | 101.4% | NAP | NAP | NAP | NAP | NAP | NAP |

TABLE 16-continued

| | | 0 D | | 3 WK | | 6 WK | | 14 WK | |
|---|---|---|---|---|---|---|---|---|---|
| Assay | Sample | mg/L | % Remaining * | mg/L | % Remaining ** | mg/L | % Remaining ** | mg/L | % Remaining ** |
| | Average | 258 | 101% | NAP | NAP | NAP | NAP | NAP | NAP |
| | Sterile 1 | 261 | 102.1% | 266.5 | 104.2% | 265.8 | 103.9% | 272.7 | 106.6% |
| | Sterile 2 | 261.1 | 102.1% | 271.0 | 106% | 268.4 | 104.9% | 264.3 | 103.4% |
| | Average | 261 | 102% | 269 | 105% | 267 | 104% | 269 | 105% |
| Lactose mg/L | Unsterile 1 | 25.78 | NAP | NAP | NAP | NAP | NAP | NAP | NAP |
| | Unsterile 2 | 25.46 | NAP | NAP | NAP | NAP | NAP | NAP | NAP |
| | Average | 25.6 | NAP | NAP | NAP | NAP | NAP | NAP | NAP |
| | Sterile 1 | 26.34 | NAP | 28.03 | NAP | 30.89 | NAP | 27.94 | NAP |
| | Sterile 2 | 27.26 | NAP | 28.19 | NAP | 28.6 | NAP | 28.14 | NAP |
| | Average | 26.8 | NAP | 28.10 | NAP | 29.7 | NAP | 28 | NAP |

\* % Remaining denotes the % loss or % increase for results calculated comparing the average results for unsterile to average sterile results to the target fortification. The assumed target fortification for 2'-FL is 200 mg/L.
\*\* % Remaining denotes % loss or % increase of 3, 6, and 14 weeks test results and is calculated comparing the average interval results to the average 0 D results.

Table 17 shows the results of sample measurements determining the levels of 6'-SL (mg/L), Lactose (mg/L), and Sialic acid (mg/L) and % remaining, as determined at 0 days, 3 weeks, 6 weeks, and 14 weeks. The data on day 0 was collected in duplicate for samples prior to sterilization (unsterile) and after sterilization (sterile), thereafter the data was collected only on the sterilized samples. A significant decrease in 6'-SL levels was observed post sterilization and throughout the testing intervals. At 14 weeks, the concentration was 2.3% of the target fortification amount. Slight discoloration was observed relative to the other test compositions.

TABLE 17

| | | 0 D | | 3 WK | | 6 WK | | 14 WK | |
|---|---|---|---|---|---|---|---|---|---|
| Assay | Sample | mg/L | % Remaining * | mg/L | % Remaining ** | mg/L | % Remaining ** | mg/L | % Remaining ** |
| 6'-SL mg/L | Unsterile 1 | 170.8 | 85.42% | NAP | NAP | NAP | NAP | NAP | NAP |
| | Unsterile 2 | 174.5 | 87.24% | NAP | NAP | NAP | NAP | NAP | NAP |
| | Average | 173 | 86.3% | NAP | NAP | NAP | NAP | NAP | NAP |
| | Sterile 1 | 10.39 | 5.195% | 10.5 | 5.249% | 10.47 | 5.234% | 4.66 | 2.330% |
| | Sterile 2 | 11 | 5.502% | 10.6 | 5.3% | 10.59 | 5.295% | 4.57 | 2.285% |
| | Average | 10.7 | 5.35% | 10.5 | 5.27% | 10.5 | 5.26% | 4.6 | 2.31% |
| Lactose mg/L | Unsterile 1 | 24.22 | NAP | NAP | NAP | NAP | NAP | NAP | NAP |
| | Unsterile 2 | 24.9 | NAP | NAP | NAP | NAP | NAP | NAP | NAP |
| | Average | 24.6 | NAP | NAP | NAP | NAP | NAP | NAP | NAP |
| | Sterile 1 | 149.4 | NAP | 152.2 | NAP | 170.5 | NAP | 149.5 | NAP |
| | Sterile 2 | 149.4 | NAP | 154.0 | NAP | 174.4 | NAP | 155.1 | NAP |
| | Average | 149 | NAP | 153 | NAP | 172 | NAP | 152 | NAP |
| Sialic acid mg/L | Unsterile 1 | 5.055 | NAP | NAP | NAP | NAP | NAP | NAP | NAP |
| | Unsterile 2 | 4.842 | NAP | NAP | NAP | NAP | NAP | NAP | NAP |
| | Average | 4.95 | NAP | NAP | NAP | NAP | NAP | NAP | NAP |
| | Sterile 1 | 83.46 | NAP | 82.89 | NAP | 98.77 | NAP | 91.10 | NAP |
| | Sterile 2 | 83.79 | NAP | 82.96 | NAP | 97.2 | NAP | 92.22 | NAP |
| | Average | 83.6 | NAP | 82.9 | NAP | 98 | NAP | 91.7 | NAP |

\* % Remaining denotes the % loss or % increase for results calculated comparing the average results for unsterile to average sterile results to the target fortification. The assumed target fortification for 2'-FL is 200 mg/L.
\*\* % Remaining denotes % loss or % increase of 3, 6, and 14 weeks test results and is calculated comparing the average interval results to the average 0 D results.

While the general inventive concepts have been illustrated by the description of various exemplary embodiments, and while the exemplary embodiments have been described in considerable detail, it is not the intention of the applicants to restrict or in any way limit the scope of the general inventive concepts or the appended claims to such detail. Additional advantages and modifications will readily appear to those skilled in the art. Therefore, the general inventive concepts are not limited to the specific details, the representative compositions and processes, and illustrative examples shown and described. Accordingly, departures may be made from such details without departing from the spirit or scope of the general inventive concepts.

What is claimed is:
1. A nutritional composition comprising:
   a human milk oligosaccharide selected from the group consisting of a fucosylated oligosaccharide, an N-acetylated oligosaccharide, and combinations thereof in an amount of 10 mg to 5000 mg per liter of the nutritional composition;
   a digestible carbohydrate in addition to the human milk oligosaccharide in an amount of from 10 mM to 150 mM of carbohydrate of the nutritional composition; and
   sodium in an amount of 10 mEq to 100 mEq of sodium per liter of the nutritional composition;
   wherein the nutritional composition does not comprise a sialylated oligosaccharide, and is an aqueous compo- sition having a pH of about 2 to about 6.5 that is self-stable for 6 months to 24 months after heat sterilization.

2. The nutritional composition of claim 1, wherein the human milk oligosaccharide is selected from 2'-fucosyllactose and lacto-N-neotetraose.

3. The nutritional composition of claim 2, wherein the human milk oligosaccharide is 2'-fucosyllactose.

4. The nutritional composition of claim 3, wherein the 2'-fucosyllactose is present in an amount of 20 mg to 4000 mg per liter of the nutritional composition.

5. The nutritional composition of claim 3 further comprising at least one neutral human milk oligosaccharide.

6. The nutritional composition of claim 3 further comprising galactooligosaccharides.

7. The nutritional composition of claim 3 further comprising at least one of protein and fat.

8. The nutritional composition of claim 3, wherein the digestible carbohydrate is selected from the group consisting of dextrose, maltodextrin, starch, isomaltulose, sucromalt, rice syrup, and rice syrup solids.

9. The nutritional composition of claim 3, wherein the digestible carbohydrate is dextrose.

10. The nutritional composition of claim 3, wherein the sodium is selected from the group consisting of sodium chloride, sodium phosphate, sodium citrate, sodium carbonate, sodium bicarbonate, sodium hydroxide, sodium ascorbate and combinations thereof.

11. The nutritional composition of claim 3 further comprising a probiotic.

12. The nutritional composition of claim 3 further comprising chloride.

13. The nutritional composition of claim 12, wherein the chloride is selected from the group consisting of sodium chloride, potassium chloride, calcium chloride, magnesium chloride, and combinations thereof.

14. The nutritional composition of claim 3 further comprising zinc.

15. The nutritional composition of claim 14, wherein the zinc is selected from the group consisting of zinc gluconate, zinc sulfate, zinc chloride, zinc citrate, zinc bicarbonate, zinc carbonate, zinc hydroxide, zinc lactate, zinc acetate, zinc fluoride, zinc bromide, zinc sulfonate, and combinations thereof.

16. The nutritional composition of claim 3 further comprising citrate.

17. The nutritional composition of claim 16, wherein the citrate is selected from the group consisting of potassium citrate, sodium citrate, zinc citrate, and combinations thereof.

* * * * *